United States Patent [19]

Irvine, Jr. et al.

[11] Patent Number: 4,637,250

[45] Date of Patent: Jan. 20, 1987

[54] APPARATUS AND METHOD FOR VISCOSITY MEASUREMENTS FOR NEWTONIAN AND NON-NEWTONIAN FLUIDS

[75] Inventors: Thomas F. Irvine, Jr.; Noh-Aeok Park, both of Stony Brook, N.Y.

[73] Assignee: State University of New York, Stony Brook, N.Y.

[21] Appl. No.: 694,747

[22] Filed: Jan. 25, 1985

[51] Int. Cl.$^4$ .............................................. G01N 11/12
[52] U.S. Cl. ............................................ 73/57; 73/54
[58] Field of Search ...................... 73/57, 54, 449, 440

[56] References Cited

U.S. PATENT DOCUMENTS

| 2,778,220 | 1/1957 | Kuhlmann et al. ...................... 73/57 |
| 3,231,738 | 1/1966 | Danforth et al. ....................... 73/448 |
| 4,388,823 | 6/1983 | Garnaud et al. ......................... 73/57 |
| 4,466,275 | 8/1984 | Thone ..................................... 73/57 |
| 4,517,830 | 5/1985 | Gunn et al. .............................. 73/57 |

FOREIGN PATENT DOCUMENTS

| 611575 | 12/1960 | Canada ..................................... 73/57 |
| 950506 | 10/1956 | Fed. Rep. of Germany ........... 73/57 |
| 2946453 | 5/1981 | Fed. Rep. of Germany ........... 73/57 |
| 751958 | 7/1956 | United Kingdom ..................... 73/57 |
| 1322672 | 7/1973 | United Kingdom ................... 73/448 |
| 1491865 | 11/1977 | United Kingdom ..................... 73/57 |

OTHER PUBLICATIONS

J. B. Irving et al, An Automatic High Pressure Viscometer, J. Phys. E (GB), vol. 4, Mar. 1971.
Lohrenz, Swift and Kurata "The Experimentally Verified Theoretical Study of the Falling Cylinder Viscometer", *A.I. Ch. E. Journal*, vol. 6, No. 4, p. 547, (Dec. 1960).
Smith, "The Plunger Rheometer-Low of Flow for a Newtonian Fluid", *J. of Inst. of Petrol.*, vol. 43, No. 404, pp. 227-230, (Aug. 1957).
F. J. Eichstadt and G. W. Swift "Theoretical Analysis of the Falling Cylinder Viscometer for Power Law and Bingham Plastic Fluids", *A.I.Ch.E*, vol. 12, No. 6, pp. 1179-1183, (1966).

*Primary Examiner*—Stewart J. Levy
*Assistant Examiner*—Hezron E. Williams
*Attorney, Agent, or Firm*—Morgan & Finnegan

[57] ABSTRACT

The present invention relates to an apparatus and method for determining the viscosity of Newtonian and non-Newtonian fluids. More particularly, the present invention relates to an apparatus and method for determining the viscosity of a fluid by measuring the time of fall of a needle through a predetermined distance of the fluid held in a container. The method further provides exact equations according to a modified power law model and Ellis model for the calculation of viscosity, shear stress and shear rate.

19 Claims, 12 Drawing Figures

FLOW CHART OF THE ELLIS MODEL CALCULATION
FOR THE FALLING NEEDLE VISCOMETER

WHERE $I_3 = \int_k^\lambda \left(\frac{\lambda^2}{r} - r\right)^\alpha r^2 dr$ $I_4 = \int_\lambda^1 \left(r - \frac{\lambda^2}{r}\right)^\alpha r^2 dr$ $I_5 = \int_k^\lambda \left(\frac{\lambda^2}{r} - r\right)^\alpha dr$ $I_6 = \int_\lambda^1 \left(r - \frac{\lambda^2}{r}\right)^\alpha dr$

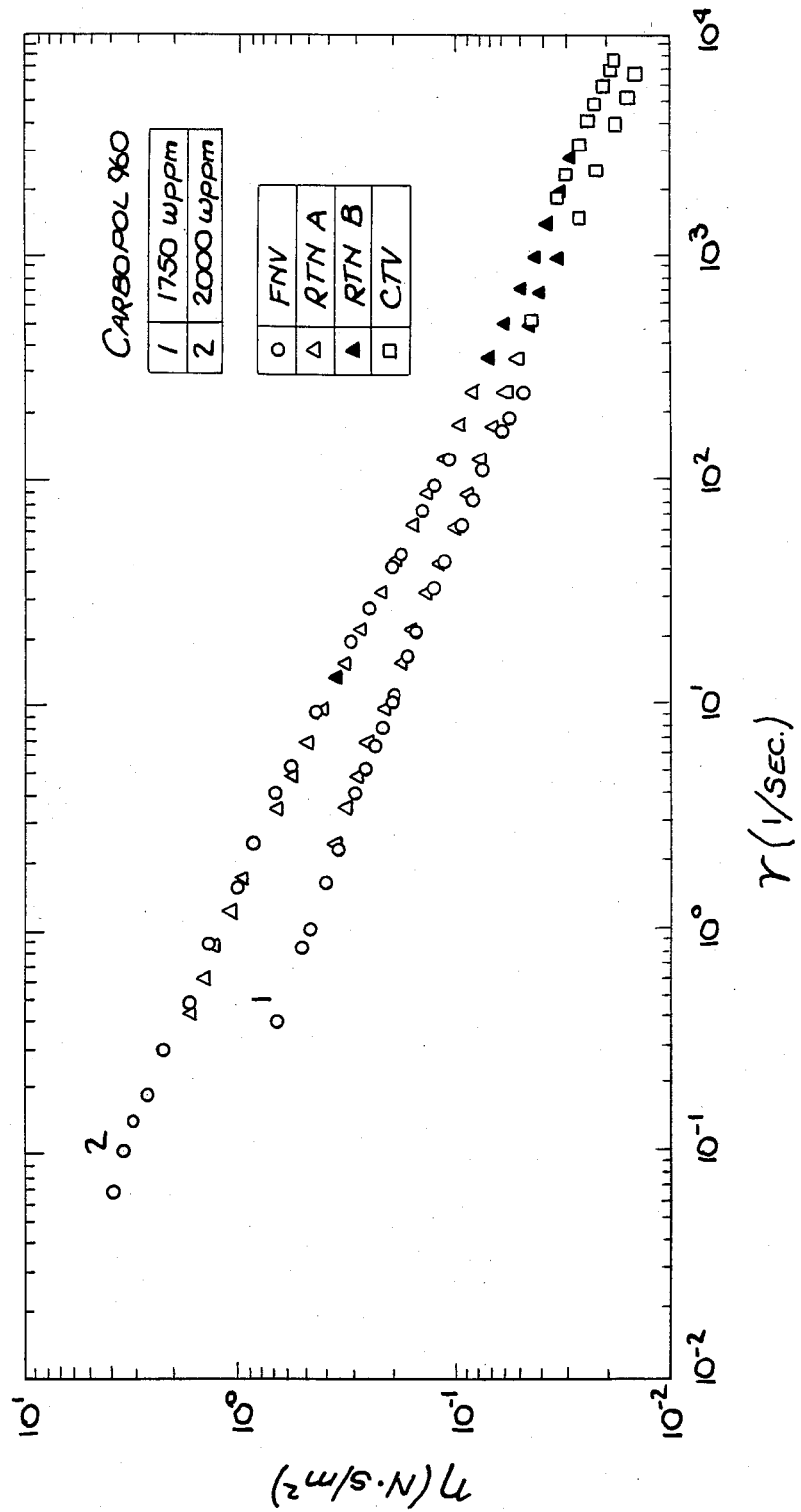

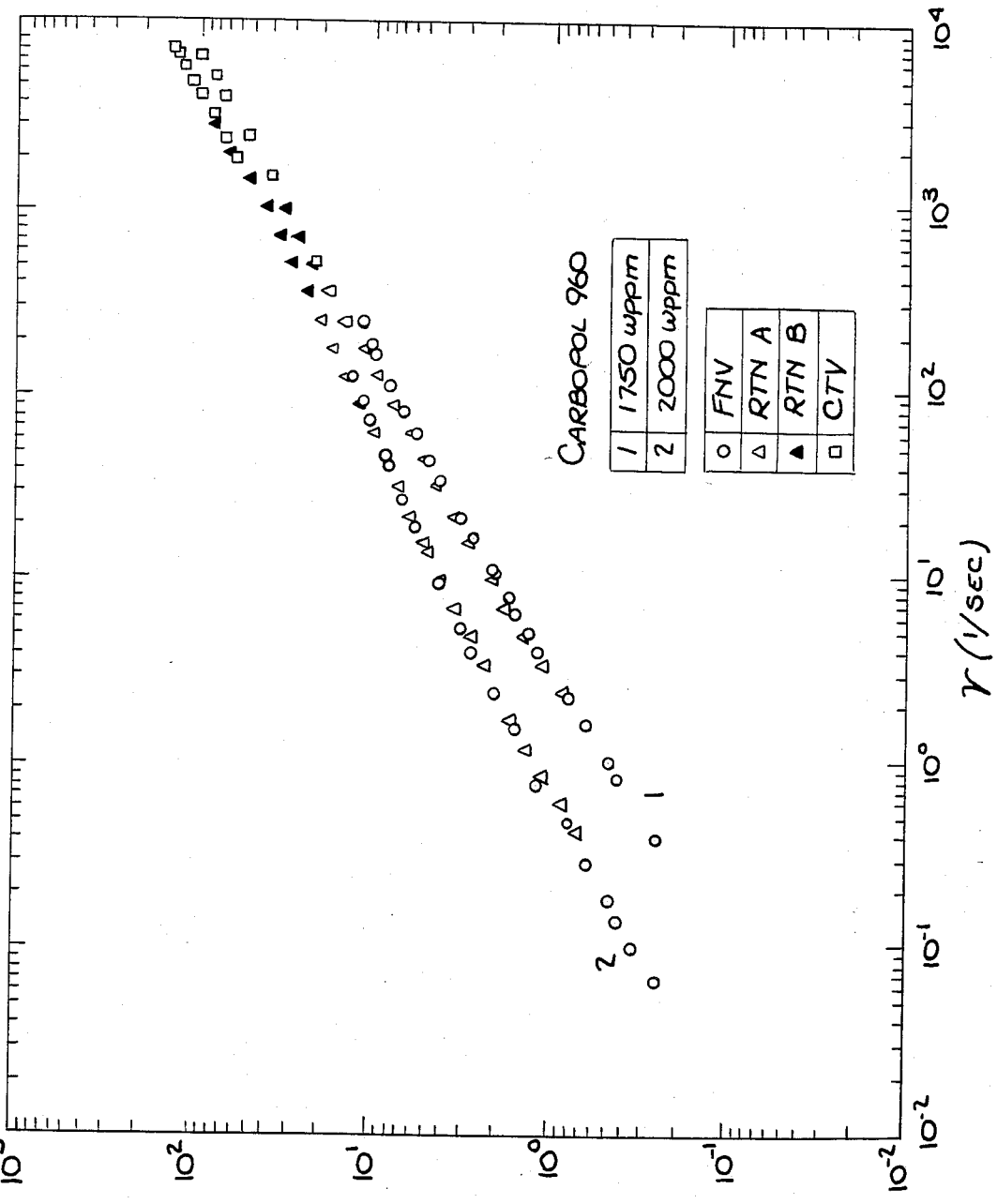
Fig. 9. Shear Stress vs. Shear Rate For Carbopol 960 1,750 wppm And 2,000 wppm Solutions

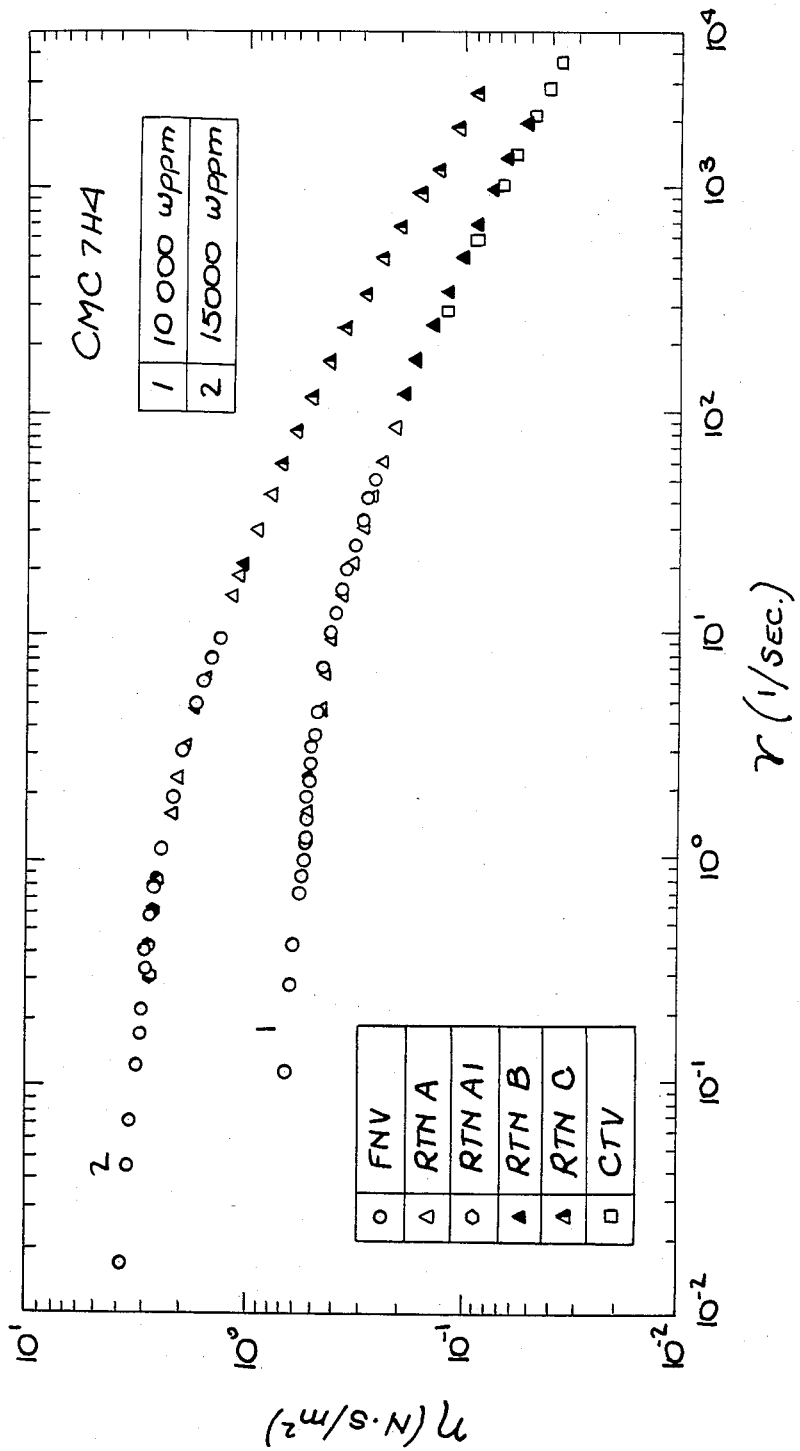

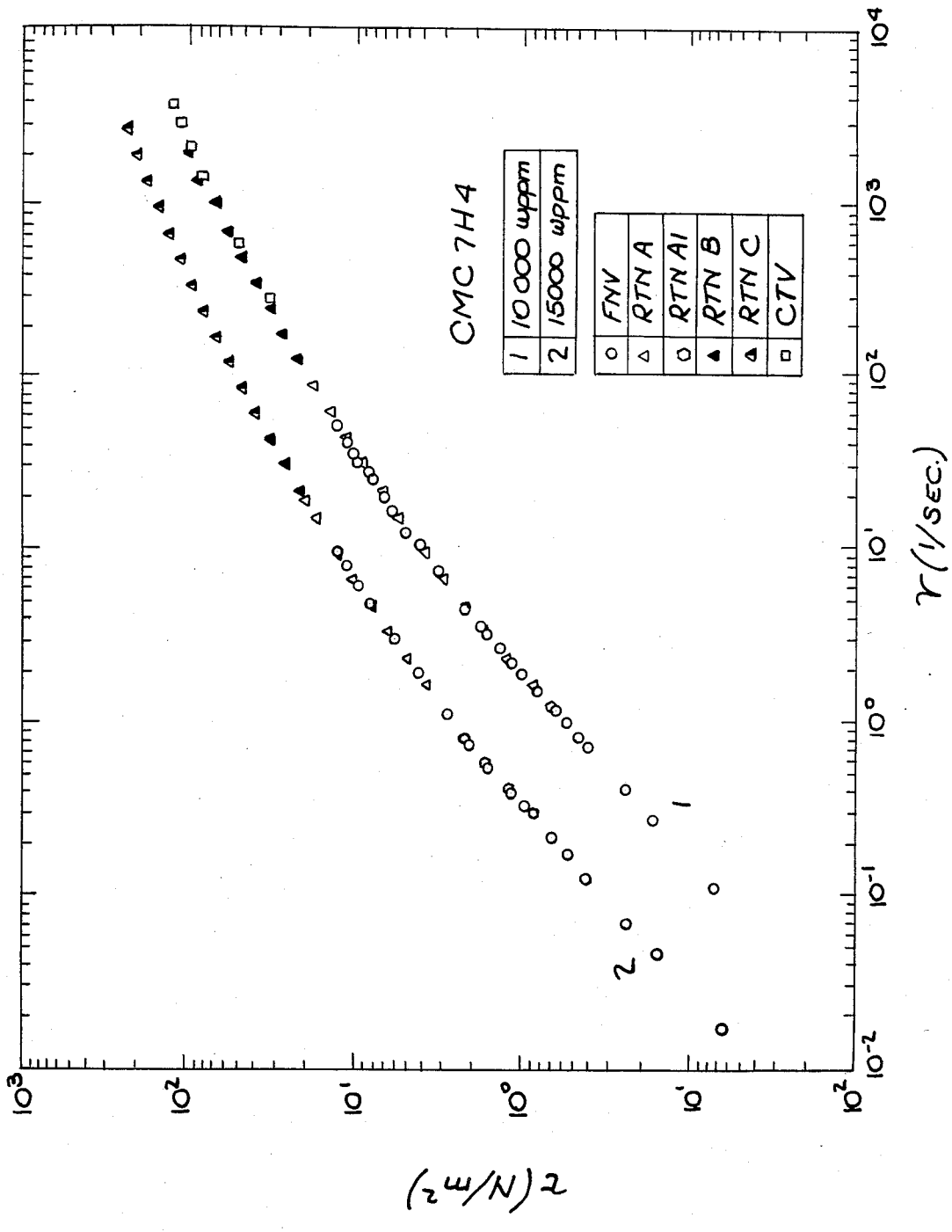
Fig. 11. Shear Stress vs. Shear Rate for CMC 7H4 10,000 wppm and 15000 wppm Solutions.

APPARATUS AND METHOD FOR VISCOSITY MEASUREMENTS FOR NEWTONIAN AND NON-NEWTONIAN FLUIDS

INTRODUCTION

The present invention relates to an apparatus and method for determining the viscosity of Newtonian and non-Newtonian fluids. More particularly, the present invention relates to an apparatus and method for determining the viscosity of a fluid by measuring the time of fall of a needle through a predetermined distance of the fluid held in a container.

BACKGROUND OF THE INVENTION

A fluid can generally be classified as ideal, Newtonian or non-Newtonian based on the behavior of the fluid under shear stress. An ideal fluid has no shear stress in a flow field and its viscosity is zero. No fluids which exhibit this type of behavior exist. In a Newtonian fluid, such as water, glycerol, the shear stress is directly proportional to the shear rate; and its viscosity is independent of the shear rate. In a non-Newtonian fluid, the shear stress is dependent on the shear rate and its viscosity may vary with the shear rate in a complex manner. See FIG. 1.

Viscosity is a measurement of the behavior of a fluid under stress. It is, therefore, important to be able to accurately determine the viscosity of a fluid in order to improve the design of pumps, stirrers, mixers, liquid transport devices, and reactors. Futhermore, the molecular weight of a polymer solution is related to its viscosity at zero shear rate and an accurate determination of the zero shear rate viscosity of a polymer solution enables one to obtain an accurate measurement of its molecular weight.

The viscosity of a fluid, $\eta$ is defined as the force in dynes per square centimeter (cm.) necessary to maintain a velocity of 1 cm. per second (sec.) between two layers of a fluid 1 cm. apart. Many methods have been developed to determine the viscosity of fluids. The earliest is the capillary tube viscometer. For a capillary tube viscometer, viscosity may be defined as:

$$\eta = \frac{\pi r^4 t p}{8 v L}$$

where v is volume in cc., t is time in sec., r is the radius in cm. of a narrow tube through which the fluid is flowing, L is the length in cm: and p is the pressure drop between length L in dynes per sq. cm.

Although this method can be used to determine the viscosity of Newtonian and non-Newtonian fluids, this suffers from many disadvantages. It is difficult to accurately measure the small pressure differences involved, precisely calibrate the diameter of the capillary tube and keep the capillary tube clean. Further, the capillary tube viscometer is only applicable for determining the viscosity at high shear rates. It cannot be used to determine viscosity at low shear rates.

Another approach is the falling sphere or falling ball viscometry first described in G.G. Stokes, *Camb. Phil. Trans.*, 9, p.8 (1851). In this method, the time, t sec., taken for a sphere d to fall through a predetermined distance L cm. in an infinite fluid medium is measured. The viscosity is then calculated in accordance with the following equation:

$$V_\infty = \frac{(\rho_s - \rho_f)gd^2}{18\eta}$$

However, in the falling sphere method, the following assumptions are made: the spheres are falling in an infinite medium, the density of the falling sphere is in a suitable range for the equation to hold true, and the sphere must be perfectly round, so that it will fall vertically through the fluid and will not veer in one direction or another or fall erratically.

In practice, spheres can only be made from a limited range of materials, such as, glass, aluminum or steel and the density cannot be adjusted. Further, very few spheres are truly round and, as a consequence, the fall through the fluid medium is not truly vertical. Moreover, a fluid must be held in a container, therefore, wall effects have to be considered. Thus, inaccuracies arise from the non-vertical fall of a sphere and a correction factor for wall effects must be applied.

Moreover, the falling sphere method does not provide an exact solution for non-Newtonian fluids because of the geometric complexities involved.

Falling cylinder and falling plunger viscometers have also been designed. See, Lohrentz, et al., *A. I. Ch. E. Journal*, 6, No. 4 p. 547–549 (1960) and G. S. Smith, *J. Inst. Pet.*, 43, p. 227–230 (1957). These are found wanting because it is difficult to construct the falling cylinder or plunger, difficult to obtain cylinders or plungers with different densities and difficult to maintain a vertical fall through the fluid. To maintain a vertical fall through the fluid, guide pins or bushings are required. Further, the eccentricity effect is very significant. Because of these problems, it is difficult to account for the systematic error in viscosity measurement by the falling cylinder or plunger method.

A rotating cylinder viscometer with two coaxial cylinders, a rotating outside cylinder and a stationary inside cylinder had been developed to measure the viscosity of non-Newtonian fluids. See Van Wazer et al., *Viscosity and Flow Measurement*, p. 47–96, Interscience Publishers, New York, 1963. However, the rotating cylinder viscometer is difficult and expensive to make. Further, it is very difficult to maintain a constant temperature in the system and evaporation of the fluid from the open-mouth container is unavoidable. These difficulties translate into unacceptably large errors in the viscosity obtained.

It is, therefore, an objective of the present invention to develop an apparatus and a method to determine accurately the viscosity of Newtonian and non-Newtonian fluids with the smallest systematic error possible.

It is a further objective to develop an apparatus and method which is inexpensive to manufacture and easy to use.

SUMMARY OF THE INVENTION.

According to the present invention an apparatus and methods for the accurate determination of the viscosity of Newtonian and non-Newtonian fluids have been developed. The apparatus is simple, easy to use and the equations for the accurate determination of the viscosities of both Newtonian and non-Newtonian fluids from the data collected by the use of the apparatus have been derived. The apparatus comprises:

a. A cylinder, of diameter D cm., for holding the fluid for which the viscosity is to be determined, on the inside wall of which a predetermined distance, L cm., is marked along the vertical axis of the cylinder, the top mark L being at least D from the top of the cylinder, and the bottom mark being at least D from the bottom of the cylinder;

b. A needle, made of tubing of material selected from the group comprising glass, aluminum and stainless steel, capable of being adjusted with thin metal wiring inserts to produce a velocity of fall of almost 0 to about 10 cm. per sec. and sealed hemispherically at both ends, having a diameter d cm., wherein d=D/d is at least 5, and a length of 1 cm., wherein 1/D is at least 2.5;

c. A funnel placed on top of the cylinder with cylindrical walls, a bottom and a spacer held at a distance above the bottom, each of the bottom and spacer having a hole in the center aligned vertically with each other, and coaxially to the vertical axis of the cylinder;

d. Means for maintaining a constant temperature in the cylinder; and e. Means for measuring the time of fall of the needle between the predetermined distance marked on the cylinder.

The cylinder may have a double wall i.e. a water jacket, with an inlet and outlet to permit the circulating of water or oil at a constant temperature. The cylinder may be equipped with thermocouples inserted into the space between the walls to monitor the temperature in the apparatus.

The time of fall may be measured by eye with a stopwatch or by electronic means.

The method of determining the viscosity of a Newtonian fluid using the apparatus described above comprise the following steps:

a. Filling a cylinder with a diameter D according to the apparatus described above with a fluid for which the viscosity is to be determined;

b. Placing a funnel with bottom and spacer and holes aligned vertically therein on top of the cylinder;

c. Activating means for maintaining a constant temperature in the fluid;

d. Inserting a needle having a diameter d and a length l, wherein b=D/d is at least 5 and l/D is at least 2.5 and adjusted to produce a velocity of fall of approximately 0 to 10 cm. per sec., into the hole in the spacer of the funnel, and held in position until the temperature of the needle is the same as that of the fluid;

e. Allowing the needle to fall through the hole on bottom of the funnel;

f. Measuring the time, t sec., taken for the needle to fall between the predetermined distance, L cm., marked on the cylinder, and g. Calculating the viscosity, by using the following equations:

$$\eta = \frac{(\rho_s - \rho_f)gd^2}{8V_\infty} \cdot \frac{b^2(\ln b - 1) + (\ln b + 1)}{b^2 + 1}$$

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

where $\rho_s$ is the density of the needle, $\rho_f$ is the density of the fluid, g is the gravity constant, d is the diameter of the needle, L is the predetermined distance of fall, t is the time of fall and b=D/d.

For non-Newtonian fluids, the time of fall, t sec., is measured for at least three different needles, i.e. with the same lengths and diameters and different densities.

Then using the data, the viscosity is calculated using the following equations derived from a modified power law model:

1. $V_\infty$ is calculated as follows:

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

l is the length of the needle, L is the predetermined distance marked on the cylinder and t, the time taken for the need to fall through L cm.

2. The flow index, n, where:

$$n = \frac{d[\ln(\rho_s - \rho_f)]}{d[\ln V_\infty]}$$

is determined from the slop of log $(\rho_s - \rho_f)$ vs. log $V_\infty$, 3. n is then used to determine the position of maximum velocity λ, by solving the integral equation:

$$\int_k^\lambda \left(\frac{\lambda^2}{r} - r\right)^{1/n} r^2 dr - \int_k^\lambda \left(r - \frac{\lambda^2}{r}\right)^{1/n} r^2 dr = 0$$

where k=1/b and r is the ratio of the coordinate to R, the radius of the cylinder.

4. λ and n are then used to solve the equation to obtain p+:

$$\int_k^\lambda \left(\frac{\lambda^2}{r} - r\right)^{1/n} dr - \int_\lambda^1 \left(r - \frac{\lambda^2}{r}\right)^{1/n} dr = \frac{1}{p^+}$$

5. The fluid consistancy K is calculated from the equation:

$$K = \left(\frac{R}{V_\infty}\right)^n \left(\frac{1}{b\lambda}\right)^2 \left(\frac{1}{p^+}\right)^n \frac{gR(\rho_s - \rho_f)}{2}$$

where g is the gravity constant, R is the radius of the cylinder.

6. The shear rate at the needle wall is than calculated from:

$$\gamma_w = \frac{2V_\infty}{d} \cdot p^+ \cdot \frac{1}{b}\left(\lambda^2 b - \frac{1}{b}\right)^{1/n}$$

7. The shear stress at the needle wall is then calculated using the equation:

$$\tau_w = \frac{gd(\rho_s - \rho_f)}{4}\left\{\left(\frac{1}{\lambda b}\right)^2 - 1\right\}$$

8. The viscosity, $\eta$, is then calculated as:

$$\eta = \frac{-\tau_w}{\gamma_w}$$

The calculation has been simplified by the use of Table I and Table II for determining $\lambda$ and $p^+$.

TABLE I $\lambda$ values of power law model with k and n.

| k | n 0.1 | 0.2 | 0.3 | 0.4 | 0.5 | 0.6 | 0.7 | 0.8 | 0.9 | 1.0 |
|---|---|---|---|---|---|---|---|---|---|---|
| 0.01 | 0.18966 | 0.32323 | 0.46355 | 0.55849 | 0.61264 | 0.64591 | 0.66844 | 0.68481 | 0.69729 | 0.70714 |
| 0.02 | 0.23931 | 0.36515 | 0.48378 | 0.56509 | 0.61487 | 0.64683 | 0.66889 | 0.68506 | 0.69745 | 0.70725 |
| 0.03 | 0.27373 | 0.39205 | 0.49749 | 0.57056 | 0.61715 | 0.64792 | 0.66949 | 0.68543 | 0.69769 | 0.70742 |
| 0.04 | 0.30091 | 0.41248 | 0.50840 | 0.57549 | 0.61947 | 0.64914 | 0.67022 | 0.68591 | 0.69802 | 0.70767 |
| 0.05 | 0.32376 | 0.42927 | 0.51774 | 0.58010 | 0.62184 | 0.65049 | 0.67106 | 0.68648 | 0.69844 | 0.70799 |
| 0.06 | 0.34368 | 0.44373 | 0.52606 | 0.58448 | 0.62425 | 0.65194 | 0.67201 | 0.68715 | 0.69894 | 0.70838 |
| 0.07 | 0.36147 | 0.45656 | 0.53367 | 0.58873 | 0.62672 | 0.65349 | 0.67306 | 0.68790 | 0.69952 | 0.70884 |
| 0.08 | 0.37766 | 0.46819 | 0.54077 | 0.59286 | 0.62923 | 0.65512 | 0.67420 | 0.68875 | 0.70017 | 0.70936 |
| 0.09 | 0.39258 | 0.47890 | 0.54747 | 0.59692 | 0.63178 | 0.65684 | 0.67543 | 0.68968 | 0.70090 | 0.70996 |
| 0.10 | 0.40647 | 0.48889 | 0.55386 | 0.60092 | 0.63438 | 0.65863 | 0.67675 | 0.69069 | 0.70171 | 0.71063 |
| 0.2 | 0.51400 | 0.56805 | 0.60917 | 0.63982 | 0.66279 | 0.68033 | 0.69401 | 0.70492 | 0.71378 | 0.72111 |
| 0.3 | 0.59505 | 0.63132 | 0.65865 | 0.67934 | 0.69526 | 0.70775 | 0.71773 | 0.72586 | 0.73259 | 0.73824 |
| 0.4 | 0.66472 | 0.68872 | 0.70676 | 0.72055 | 0.73132 | 0.73991 | 0.74688 | 0.75265 | 0.75748 | 0.76157 |
| 0.5 | 0.72994 | 0.74327 | 0.75472 | 0.76355 | 0.77050 | 0.77611 | 0.78071 | 0.78455 | 0.78779 | 0.79057 |
| 0.6 | 0.78712 | 0.79617 | 0.80296 | 0.80822 | 0.81239 | 0.81577 | 0.81856 | 0.82091 | 0.82290 | 0.82462 |
| 0.7 | 0.84328 | 0.84804 | 0.85161 | 0.85438 | 0.85659 | 0.85838 | 0.85988 | 0.86113 | 0.86220 | 0.86313 |
| 0.8 | 0.89720 | 0.89919 | 0.90068 | 0.90185 | 0.90277 | 0.90353 | 0.90416 | 0.90469 | 0.90514 | 0.90554 |
| 0.9 | 0.94339 | 0.94810 | 0.95016 | 0.95044 | 0.95066 | 0.95083 | 0.95098 | 0.95111 | 0.95122 | 0.95131 |

TABLE II p+ values of power law model with k and n.

| k | n 0.1 | 0.2 | 0.3 | 0.4 | 0.5 |
|---|---|---|---|---|---|
| 0.01 | 0.25638E − 2 | 0.32395E − 2 | 0.85161E − 2 | 0.28058E − 1 | 0.74431E − 1 |
| 0.02 | 0.13279E − 1 | 0.15647E − 1 | 0.32908E − 1 | 0.77032E − 1 | 0.15411 |
| 0.03 | 0.37118E − 1 | 0.40048E − 1 | 0.72174E − 1 | 0.13951 | 0.23933 |
| 0.04 | 0.80138E − 1 | 0.78877E − 1 | 0.12605 | 0.21368 | 0.33049 |
| 0.05 | 0.14990 | 0.13456 | 0.19473 | 0.29895 | 0.42803 |
| 0.06 | 0.25580 | 0.20966 | 0.27872 | 0.39528 | 0.53242 |
| 0.07 | 0.40963 | 0.30700 | 0.37878 | 0.50289 | 0.64415 |
| 0.08 | 0.62598 | 0.42971 | 0.49592 | 0.62227 | 0.76379 |
| 0.09 | 0.92314 | 0.58132 | 0.63130 | 0.75403 | 0.89191 |
| 0.1 | 0.13239E + 1 | 0.76579 | 0.78640 | 0.89894 | 0.10292E + 1 |
| 0.2 | 0.22373E + 2 | 0.58060E + 1 | 0.39117E + 1 | 0.33356E + 1 | 0.30928E + 1 |
| 0.3 | 0.22813E + 3 | 0.26920E + 2 | 0.13065E + 2 | 0.91546E + 1 | 0.74297E + 1 |
| 0.4 | 0.22543E + 4 | 0.11437E + 3 | 0.40469E + 2 | 0.23806E + 2 | 0.17250E + 2 |
| 0.5 | 0.26968E + 5 | 0.52500E + 3 | 0.13229E + 3 | 0.65027E + 2 | 0.42091E + 2 |
| 0.6 | 0.48203E + 6 | 0.29857E + 4 | 0.50738E + 3 | 0.20357E + 3 | 0.11629E + 3 |
| 0.7 | 0.17646E + 8 | 0.25463E + 5 | 0.26423E + 4 | 0.82565E + 3 | 0.40513E + 3 |
| 0.8 | 0.25493E + 10 | 0.47977E + 6 | 0.25122E + 5 | 0.55621E + 4 | 0.22197E + 4 |
| 0.9 | 0.11319E + 14 | 0.66126E + 8 | 0.10869E + 7 | 0.13467E + 6 | 0.37934E + 5 |

| k | n 0.6 | 0.7 | 0.8 | 0.9 | 1.0 |
|---|---|---|---|---|---|
| 0.01 | 0.14984 | 0.24563 | 0.35039 | 0.45517 | 0.55461 |
| 0.02 | 0.25590 | 0.36881 | 0.48189 | 0.58871 | 0.68633 |
| 0.03 | 0.35726 | 0.47894 | 0.59516 | 0.70150 | 0.79661 |
| 0.04 | 0.45884 | 0.58508 | 0.70188 | 0.80648 | 0.89862 |
| 0.05 | 0.56274 | 0.69073 | 0.80642 | 0.90838 | 0.99715 |
| 0.06 | 0.67022 | 0.79779 | 0.91105 | 0.10096E + 1 | 0.10946E + 1 |
| 0.07 | 0.78219 | 0.90748 | 0.10172E + 1 | 0.11116E + 1 | 0.11925E + 1 |
| 0.08 | 0.89945 | 0.10207E + 1 | 0.11258E + 1 | 0.12154E + 1 | 0.12918E + 1 |
| 0.09 | 0.10226E + 1 | 0.11383E + 1 | 0.12376E + 1 | 0.13219E + 1 | 0.13932E + 1 |
| 0.1 | 0.11524E + 1 | 0.12609E + 1 | 0.13534E + 1 | 0.14316E + 1 | 0.14974E + 1 |
| 0.2 | 0.29703E + 1 | 0.29000E + 1 | 0.28554E + 1 | 0.28246E + 1 | 0.28019E + 1 |
| 0.3 | 0.64827E + 1 | 0.58901E + 1 | 0.54859E + 1 | 0.51930E + 1 | 0.49711E + 1 |
| 0.4 | 0.13894E + 2 | 0.11895E + 2 | 0.10580E + 2 | 0.96560E + 1 | 0.89729E + 1 |
| 0.5 | 0.31357E + 2 | 0.25347E + 2 | 0.21576E + 2 | 0.19016E + 2 | 0.17177E + 2 |

TABLE II-continued

| | p+ values of power law model with k and n. | | | |
|---|---|---|---|---|
| 0.6 | 0.79560E + 2 | 0.60453E + 2 | 0.49092E + 2 | 0.41692E + 2 | 0.36548E + 2 |
| 0.7 | 0.25018E + 3 | 0.17654E + 3 | 0.13557E + 3 | 0.11020E + 3 | 0.93262E + 2 |
| 0.8 | 0.11924E + 4 | 0.76182E + 3 | 0.54255E + 3 | 0.41594E + 3 | 0.33584E + 3 |
| 0.9 | 0.16128E + 5 | 0.87204E + 4 | 0.54816E + 4 | 0.38119E + 4 | 0.28469E + 4 |

Another method to calculate the viscosity is by using equations derived from the Ellis model as follows:

1. Determine $\tau$ and $\eta$ from the data obtained for at least three different needles using the procedure described above. The densities of the needles should be adjusted to proximate the density of the fluid.

2. Plot log $\eta$ vs. $\tau$. The value of $\eta_o$ is determined from the ordinate where $p=0$.

3. Determine $\alpha$ from the slope of log $V_\infty$ vs.

$$\log(\rho_s - \rho_f).$$

$$\alpha = \frac{d[\ln V_\infty]}{d[\ln(\rho_s - \rho_f)]}$$

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

4. Determine $G_o$ as follows:

$$G_o = \frac{\eta_o V_\infty}{gd^2(\rho_s - \rho_f)}$$

and solve the equation:

$$\int_k^\lambda \left(\frac{\lambda^2}{r} - r\right)^\alpha r^2 dr - \int_\lambda^1 \left(r - \frac{\lambda^2}{r}\right)^\alpha r^2 dr +$$

$$\frac{(k^2 - 1)(k^2 + 1 - 2\lambda^2)}{32G_o\lambda^2 + 2(2\lambda^2 \ln k + 1 - k^2)} \left[ \int_k^\lambda \left(\frac{\lambda^2}{r} - r\right)^\alpha dr - \int_\lambda^1 \left(r - \frac{\lambda^2}{r}\right)^\alpha dr \right] = 0$$

5. Calculate:

$$p^+ = \frac{1 + \frac{1}{G_o}\left(\frac{2\lambda^2 \ln k + 1 - k^2}{16\lambda^2}\right)}{\int_k^\lambda \left(\frac{\lambda^2}{r} - r\right)^\alpha dr - \int_\lambda^1 \left(r - \frac{\lambda^2}{r}\right)^\alpha dr}$$

6. Calculate:

$$\tau_{\frac{1}{2}} = \left[\left(\frac{R}{\eta_o V_\infty p^+}\right)\left\{\left(\frac{k}{\lambda}\right)^2 \frac{(\rho_s - \rho_f)gR}{2}\right\}^\alpha\right]^{1/(\alpha - 1)}$$

$\tau_{\frac{1}{2}}$ being the value of shear stress at $\eta = \eta_o/2$.

7. The shear stress at the needle wall is calculated from:

$$\tau_w = \frac{k\left\{\left(\frac{k}{\lambda}\right)^2 - 1\right\} gR(\rho_s - \rho_f)}{2}$$

8. The shear rate at the needle wall is $$\gamma_w = \frac{V_\infty}{R}\left\{E \cdot Q^{1/\alpha} \cdot \left(\frac{\lambda^2}{k} - k\right) + E \cdot Q \cdot \left(\frac{\lambda^2}{k} - k\right)^\alpha\right\}$$

where $E = \frac{R\tau_{\frac{1}{2}}}{\eta_o V_\infty}$ $$Q = \left\{\left(\frac{k}{\lambda}\right)^2 \frac{(\rho_s - \rho_f)gR}{2\tau_{\frac{1}{2}}}\right\}^\alpha$$

9. The viscosity is calculated from:

$$\eta = \frac{(-\tau_w)}{\gamma_w}$$

BRIEF DESCRIPTION OF THE DRAWINGS

FIG. 8 is a plot of viscosity vs. shear rate comparing the results obtained for Carbopol 960 solutions by the falling needle viscometer (FNV), the rotating cylinder viscometer (RTN) and the capillary tube viscometer (CTV).

FIG. 9 is a plot of shear stress vs. shear rate comparing the results obtained for Carbopol 960 solutions by the falling needle viscometer (FNV), the rotating cylinder viscometer (RTN) and the capillary tube viscometer (CTV).

FIG. 10 is a plot of viscosity vs. shear rate for CMC 7H4 solutions comparing the results obtaied by the falling needle viscometer (FNV), the rotating cylinder viscometer (RTN) and the capillary tube viscometer (CTV).

FIG. 11 is a plot of shear stress vs. shear rate for CMC 7H4 solutions comparing the results obtaied by the falling needle viscometer (FNV), the rotating cylinder viscometer (RTN) and the capillary tube viscometer (CTV).

DETAILED DESCRIPTION OF THE INVENTION

Figure 1:
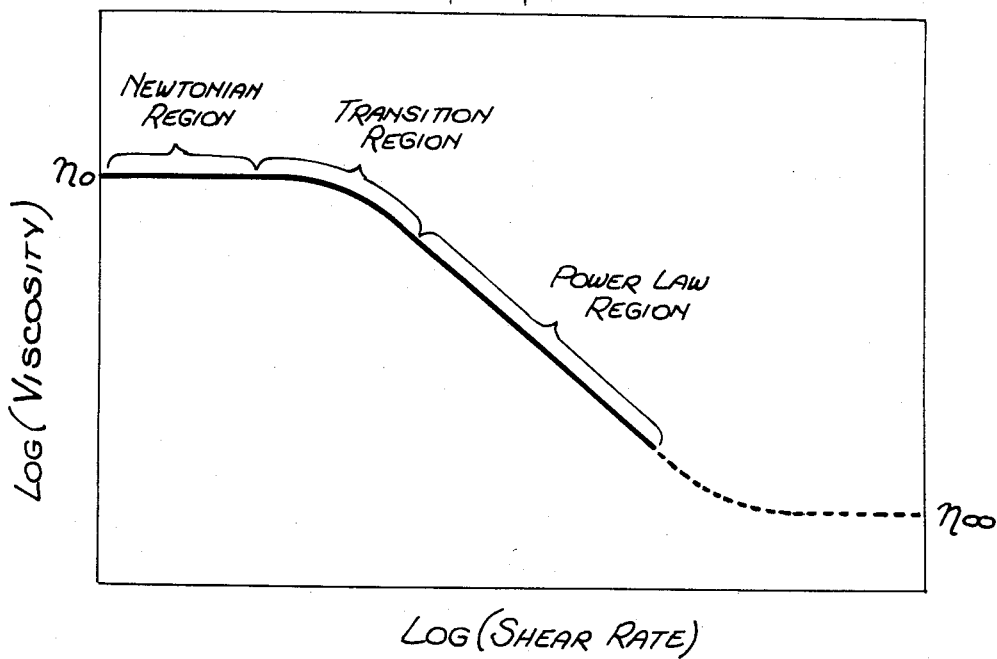
FIG. 1 is a plot on log-log graph paper of the viscosity vs. the shear rate for a non-Newtonian fluid. It can be observed that in the low shear rate region, the fluid behaves like a Newtonian fluid and the viscosity is independent of the shear rate. In the power law region, log viscosity is linear to log shear rate. In the transition region, the relation of viscosity to shear rate is complex.
Figure 2:
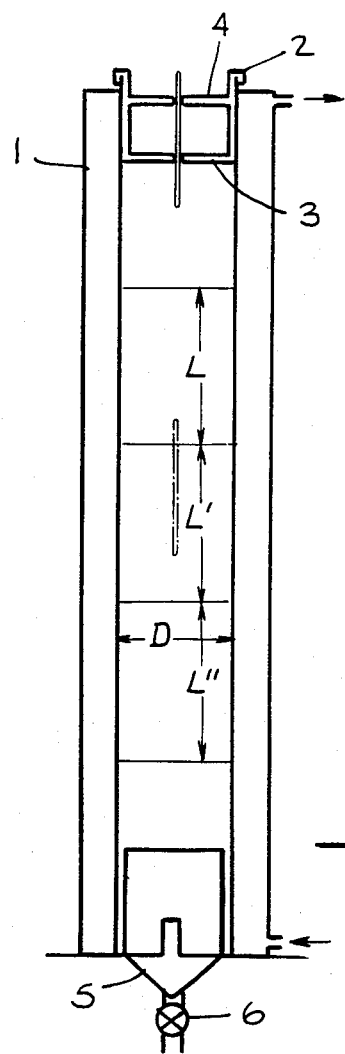
FIG. 2 is a schematic representation of the falling needle viscometer of the present invention. Cylinder (*1) is a double walled container of internal diameter D cm. having a jacket with an inlet and an outlet so that liquid can be circulated to maintain a constant temperature. On the inside wall of the cylinder, predetermined distances L, L', L" are marked. A funnel (*2) is inserted on top of the cylinder (*1). The funnel has a cylindrical side wall with a bottom (*3) and a spacer (*4). The bottom (*3) and the spacer (*4) each contain a hole coaxial with the vertical axis of the cylinder. A needle collector (*5) is situated at the bottom of the cylinder (*1) for retrieval of the needle(s) after the experiment has been finished. A drain valve (*6,) is included on the bottom of the cylinder to permit easy drainage of its contents.
Figure 3:
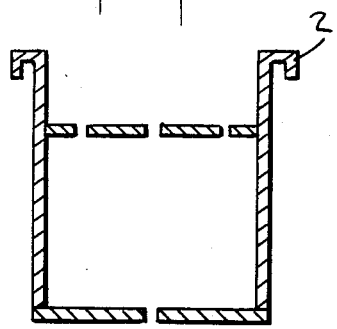
FIG. 3 is a schematic representation of a modified funnel where additional holes are provided on the spacer to accomodate more than one needle. This permits reserve needles to be placed on the funnel for these to be stabilized at the temperature of the fluid for which the viscosity is to be determined.
Figure 4A:
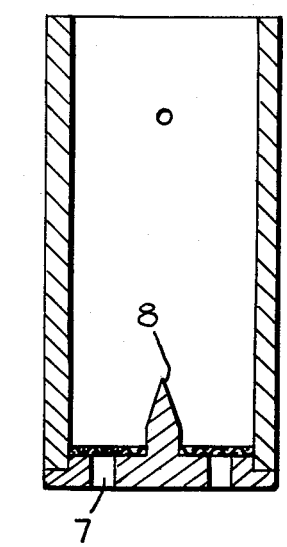
FIG. 4 is a detailed schematic representation of the needle collector (*5) in FIG. 1. A holder with cylindrical side wall and a bottom with drain-holes (*7) and a deflector (*8). The purpose of the deflector (*8) is to deflect the falling needle so that it will fall gently against the bottom and side walls. A fine net (*9) covers the bottom of the needle collector to prevent the needles from falling into the drain holes. Six holes are provided around the top of the wall of the needle collector to allow easy retrieval of the needle(s) by means of a hooking device.
Figure 4B:
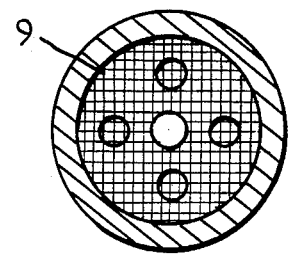
Figure 5:
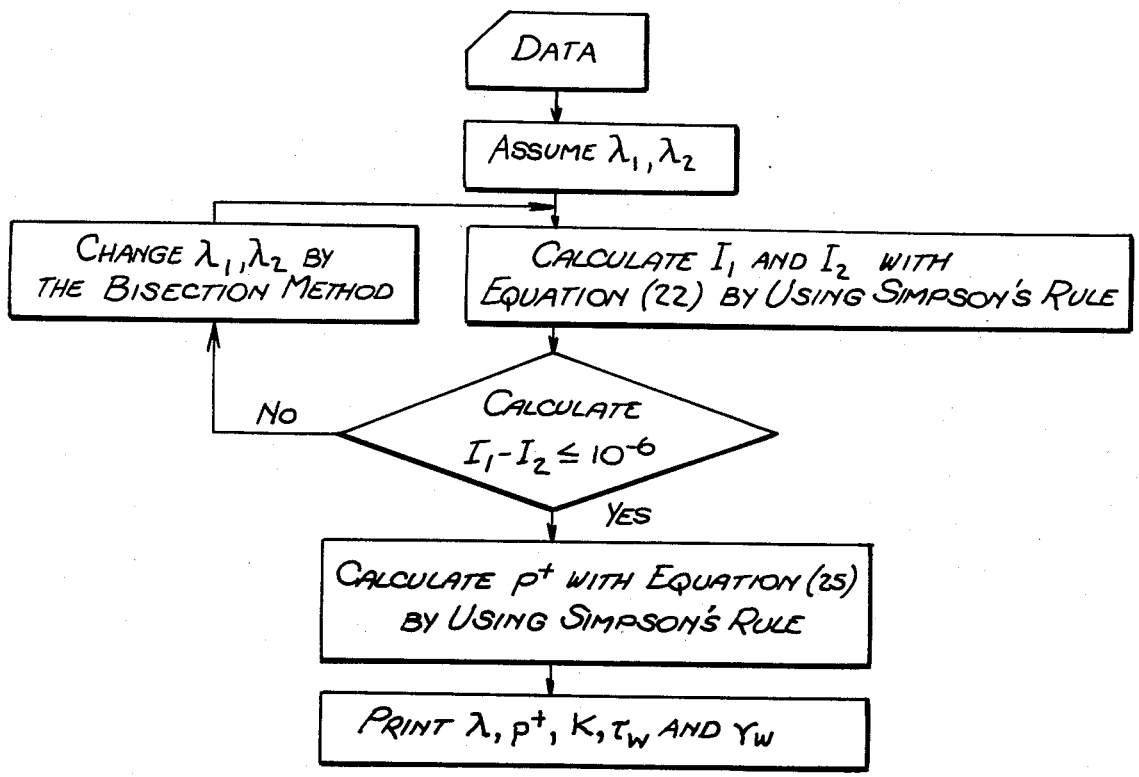
FIG. 5 is the flow chart for calculating the viscosity of a non-Newtonian fluid in accordance with the modified power law model after the time of fall has been measured for a needle through a distance L through the fluid.
Figure 6:
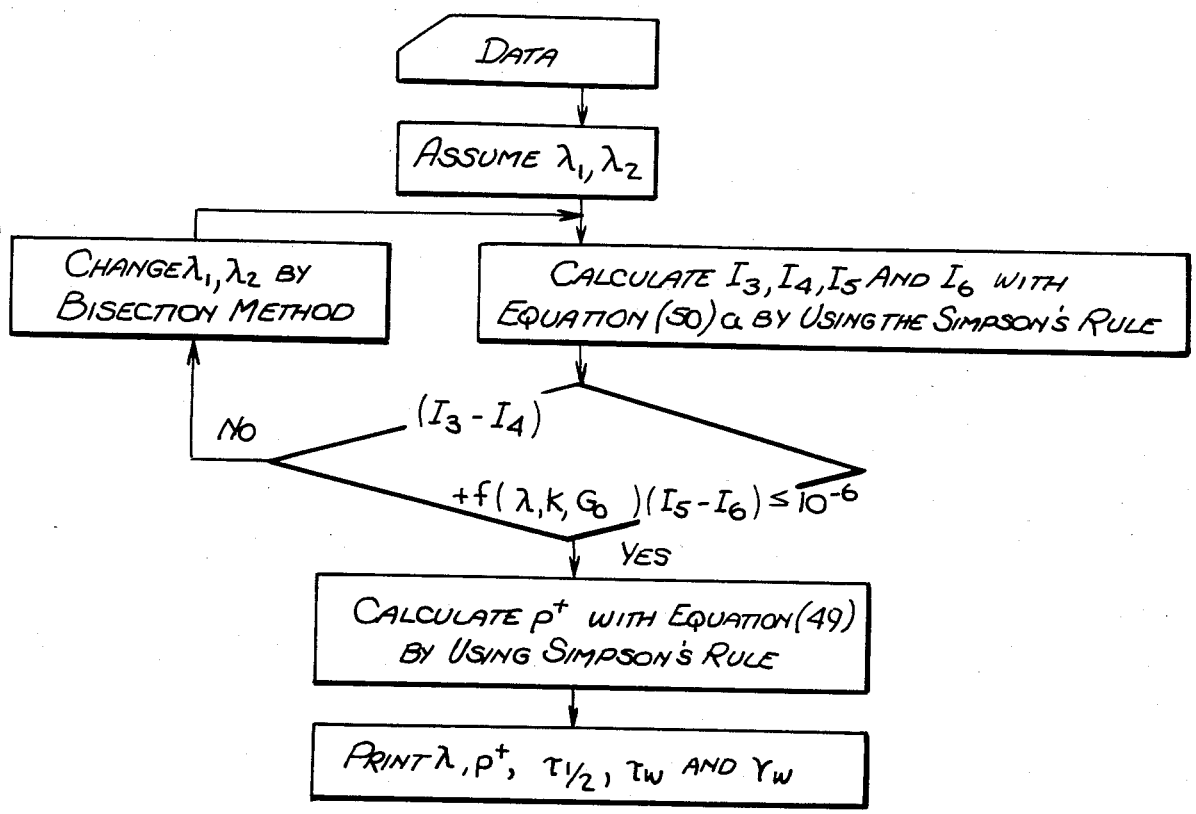
FIG. 6 is the flow chart for calculating the viscosity of a non-Newtonian fluid according to the Ellis model.

According to the present invention, an apparatus and method has been developed to determine the viscosity of Newtonian and non-Newtonian fluids. The apparatus has the following advantages:

1. It is simple to construct, comprising only four elements: a cylinder, a needle, means for controlling the temperature and means for measuring the time of fall of the needle.

2. The density of the falling needle can be adjusted so that a velocity of fall of almost 0 cm. per sec. to about 10 cm. per sec. can be obtained.

3. Since the needle is adjusted with weights on one end, the needle falls vertically and complicated devices for ensuring vertical descent are not needed.

4. The eccentricity effects can be ignored due to the large ratio of the cylinder diameter to the needle diameter.

5. It is easier to determine the zero shear rate viscosity, the shear stress and shear rate at the needle wall using the apparatus and method according to the present invention.

The apparatus for determining the viscosity of both Newtonian and non-Newtonian fluids comprises:

a. A cylinder, of diameter D for holding a fluid for which the viscosity is to be determined, on the wall of which a predetermined distance L cm. is marked along the vertical axis of the cylinder, the top mark being at least D from the top of the cylinder and the bottom mark being at least D from the bottom of the cylinder;

b. A needle made of tubing of material selected from the group comprising glass, aluminum and stainless steel capable of being adjusted with thin metal wire inserts to produce a velocity of fall of almost 0 to about 10 cm. per sec. and sealed hemispherically at both ends, having a diameter d cm., and a length l cm., wherein b=D/d is at least 5 and l/D is at least 2.5;

c. A funnel, placed on top of the cylinder, having cylindrical walls, a bottom and a spacer held at a distance above the bottom, said bottom and spacer having a hole in the center aligned vertically with each other and coaxial to the vertical axis of the cylinder;

d. Means for maintaining a constant temperature in the cylinder and the fluid; and e. Means for measuring the time of fall of the needle between the predetermined distance L cm. marked on the cylinder.

The cylinder is preferably made of transparent material, such as glass or plexiglass. A distance of L cm. is marked on the inside wall of the cylinder or means such as a photoelectronic device or a magnetic sensing device, capable of marking off a predetermined distance L cm., or predetermined distances, along the vertical axis of the cylinder is provided. Several predetermined distances, i.e. L, L', L" may be marked on the cylinder to provide more accurate determinations of the velocity of fall of a needle. It is important that the temperature of the cylinder be maintained at a constant temperature since the viscosity of a fluid is very sensitive to temperature changes. The temperature of the entire system can be maintained by immersion in a constant temperature bath. Preferably, the cylinder is constructed to have a double wall with an inlet and outlet into the double wall for circulating water or other fluids from a constant temperature bath.

The needles may be solid. However, it has been found that for measuring the viscosity of non-Newtonian fluids, it is important to be able to calibrate the density of the needle to obtain a velocity of fall of between almost 0 to about 10 cm. per sec. Therefore, it has been found to be preferable to make the needles of glass, aluminum or stainless steel tubing. Then the density can be adjusted by the insertion of small sections of thin metal wiring such as lead or solder wiring into the tubing and then sealing both ends of the tubing with heat or epoxy to provide hemispherical ends. It has been found that epoxy naturally forms hemispherical ends and is preferred.

Four double wall cylinders were constructed. Each of the double wall cylinders was constructed as follows: The inside cylinder was made of a precision glass tube with a preset diameter and welded to a drain valve. The outside cylinder was made of a plexiglass tube with a diameter larger than the diameter of the glass cylinder. The top edges of the glass cylinder and the plexiglass cylinder were sealed with two rubber o-rings and two plexiglass rings. The bottom edges of the cylinders were sealed with another set of rubber o-rings and two plexiglass rings. The double-walled unit so formed was provided with an inlet and an outlet for circulating water from a constant temperature water bath. The dimensions of the inner glass cylinders for the four double wall cylinders are shown in Table III.

TABLE III

| Cylinder | length | inside diameter | Distance L cm marked on inside wall of cylinder |||||||
|---|---|---|---|---|---|---|---|---|---|---|
| | | | Top to Section 1 | \multicolumn{6}{c|}{Sections} | Bottom |
| | | | | 1 | 2 | 3 | 4 | 5 | 6 | |
| A | 64.7 | 2.000 | 10.16 | 10.0795 | 10.0333 | 10.0482 | 10.0233 | 10.033 | 0 | 4.45 |
| B | 64.7 | 3.998 | 10.16 | 10.0795 | 10.0333 | 10.0482 | 10.0233 | 10.033 | 0· | 4.45 |
| C | 68.4 | 5.080 | 5.04 | 10.0510 | 10.0606 | 10.0552 | 10.0387 | 10.0485 | 10.0532 | 3.07 |
| D | 68.3 | 6.665 | 5.01 | 10.0480 | 10.0453 | 10.0571 | 10.0251 | 10.0241 | 10.0533 | 3.04 |

Two types of needles were constructed from glass tubing and stainless steel hypodermic needles. The densities of the needles were adjusted by inserting different weights of metal wiring such as resin core solder. The ends of the needles were sealed with epoxy to produce hemispherical ends. The density of each needle was determined by measuring the weight and the volume. Needles with a diameter of about 0.16 cm., a length of about 10 cm. and a density ranging from about 1 g per cc. to about 4.5 g per cc. were made.

It is important to keep the downward falling motion of the needles vertical and parallel to the axis of the cylinder. A needle funnel was constructed from plexiglass consisting of two discs with center holes, a distance apart attached to the inside of a circular tube. The center holes were slightly larger than the diameter of the needles. The holes in the funnel allowed air to escape. Evaporation of fluid from the cylinder was prevented by covering the top of the system with a cap.

A needle collector was constructed and inserted into the bottom of the cylinder. The needle collector is not essential to the measurement of viscosity but is used as a convenient means for retrieving the needles without loss of fluid. The needle collector was made to have a deflector in the form of a short pointed rod stuck to the bottom of the needle collector. This deflects the fall of the needle so that it will fall gently against the bottom and the side wall. The bottom of the needle collector was provided with drain holes and a wire net to prevent the needles from falling through the drain.

The method of determining the viscosity of Newtonian fluids using the apparatus described above comprises:

a. Filling the cylinder with a fluid for which the viscosity is to be determined;
b. Placing the funnel on top of the cylinder;
c. Activating means for maintaining a constant temperature in the cylinder and the fluid;
d. Inserting a needle into the hole of the spacer of the funnel;
e. Allowing the temperature of the needle to reach the temperature of the fluid;
f. Allowing the needle to fall through the hole on the bottom of the funnel;
g. Measuring the time in t sec. taken for the needle to fall between predetermined distance L cm. marked on the inside wall of the cylinder; and
h. Calculating the viscosity, n, by using the following equations:

$$\eta = \frac{(\rho_s - \rho_f)gd^2}{8V_\infty} \cdot \frac{b^2(\ln b - 1) + (\ln b + 1)}{b^2 + 1}$$

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

where
η = viscosity
$\rho_s$ = density of needles
$\rho_f$ = density of fluid
g = gravity constant
d = diameter of needle
L = predetermined distance
l = length of needle
t = time of fall in sec.
b = D/d = internal diameter of cylinder/diameter of needle.

The method for determining the viscosities of non-Newtonian fluids is determined by modifying the above procedure as follows:

The time of fall is measured for at least three needles of varying density, with the same diameter and length.

The viscosity is calculated in accordance with the modified power law model as follows:

1. $V_\infty$ is calculated as follows:

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

where L is the predetermined distance marked on the cylinder and t is the time taken for the needle to fall through L cm.

2. The flow index, n, where:

$$n = \frac{d[\ln(\rho_s - \rho_f)]}{d[\ln V_\infty]}$$

is determined from the slope of $\log(\rho_s - \rho_f)$ vs. $\log V_\infty$ 3. n is then used to determine the position of maximum velocity λ, by solving the integral equation:

$$\int_k^\lambda \left(\frac{\lambda^2}{r} - r\right)^{1/n} r^2 dr - \int_\lambda^1 \left(r - \frac{\lambda^2}{r}\right)^{1/n} r^2 dr = 0$$

where $= 1/b$ and $r$ is the ratio of the coordinate to R, the radius of the cylinder.

4. $\lambda$ and $n$ are then used to solve the equation to obtain $p^+$:

$$\int_k^\lambda \left(\frac{\lambda^2}{r} - r\right)^{1/n} dr - \int_\lambda^1 \left(r - \frac{\lambda^2}{r}\right)^{1/n} dr = \frac{1}{p^+}$$

5. The fluid consistancy K is calculated from the equation:

$$K = \left(\frac{R}{V_\infty}\right)^n \left(\frac{1}{b\lambda}\right)^2 \left(\frac{1}{p^+}\right)^n \frac{gR(\rho_s - \rho_f)}{2}$$

where g is the gravity constant, R is the radius of the cylinder.

6. The shear rate at the needle wall is then calculated from:

$$\gamma_w = \frac{2V_\infty}{d} \cdot p^+ \cdot \frac{1}{b} \left(\lambda^2 b - \frac{1}{b}\right)^{1/n}$$

7. The shear stress at the needle wall is then calculated using the equation:

$$\tau_w = \frac{gd(\rho_s - \rho_f)}{4} \left\{ \left(\frac{1}{\lambda b}\right)^2 - 1 \right\}$$

8. The viscosity, n, is then calculated as:

$$\eta = \frac{(-\tau_w)}{\gamma_w}$$

Another method to calculate the viscosity is by using equations derived from the Ellis model as follows:

1. Determine $\tau$ and $\eta$ from the data obtained for at least three different needles using the procedure described above. The densities of the needles should be adjusted to proximate the density of the fluid.

2. Plot log $\eta$ vs. $\tau$. The value of $\rho_o$ is determined from the ordinate where $\tau = 0$.

3. Determine a from the slope of log $V_\infty$ vs. $\log(\rho_s - \rho_f)$.

$$\alpha = \frac{d[\ln V_\infty]}{d[\ln(\rho_s - \rho_f)]}$$

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

-continued $$C_w = 1 - \frac{2.104}{b} + \frac{2.09}{b^3}$$

4. Determine $G_o$ as follows:

$$G_o = \frac{\eta_o V_\infty}{gd^2(\rho_s - \rho_f)}$$

and solve the equation:

$$\int_k^\lambda \left(\frac{\lambda^2}{r} - r\right)^\alpha r^2 dr - \int_\lambda^1 \left(r - \frac{\lambda^2}{r}\right)^\alpha r^2 dr +$$

$$\frac{(k^2 - 1)(k^2 + 1 - 2\lambda^2)}{32 G_o \lambda^2 + 2(2\lambda^2 \ln k + 1 - k^2)} \left[ \int_k^\lambda \left(\frac{\lambda^2}{r} - r\right)^\alpha dr - \int_\lambda^1 \left(r - \frac{\lambda^2}{r}\right)^\alpha dr \right] = 0$$

5. Calculate:

$$p^+ = \frac{1 + \frac{1}{G_o}\left(\frac{2\lambda^2 \ln k + 1 - k^2}{16\lambda^2}\right)}{\int_k^\lambda \left(\frac{\lambda^2}{r} - r\right)^\alpha dr - \int_\lambda^1 \left(r - \frac{\lambda^2}{r}\right)^\alpha dr}$$

6. Calculate:

$$\tau_{\frac{1}{2}} = \left[ \left(\frac{R}{\eta_o V_\infty p^+}\right) \left\{ \left(\frac{k}{\lambda}\right)^2 \frac{(\rho_s - \rho_f)gR}{2} \right\}^\alpha \right]^{1/(\alpha-1)}$$

$\rho_{\frac{1}{2}}$ being the value of shear stress at $\eta = \eta_o/2$.

7. The shear stress at the needle wall is calculated from:

$$\tau_w = \frac{k\left\{\left(\frac{k}{\lambda}\right)^2 - 1\right\} gR(\rho_s - \rho_f)}{2}$$

8. The shear rate at the needle wall is $$\gamma_w = \frac{V_\infty}{R} \left\{ E \cdot Q^{1/\alpha} \cdot \left(\frac{\lambda^2}{k} - k\right) + E \cdot Q \cdot \left(\frac{\lambda^2}{k} - k\right)^\alpha \right\}$$

where $E = \frac{R\tau_{\frac{1}{2}}}{\eta_o V_\infty}$ $$Q = \left\{ \left(\frac{k}{\lambda}\right)^2 \frac{(\rho_s - \rho_f)gR}{2\tau_{\frac{1}{2}}} \right\}^\alpha$$

9. The viscosity is calculated from:

$$\eta = \frac{(-\tau_w)}{\gamma_w}$$

The values for λ and p+ have been calculated for varying k and n values for the modified power law model and can be obtained from Tables I and II.

Figure 7:
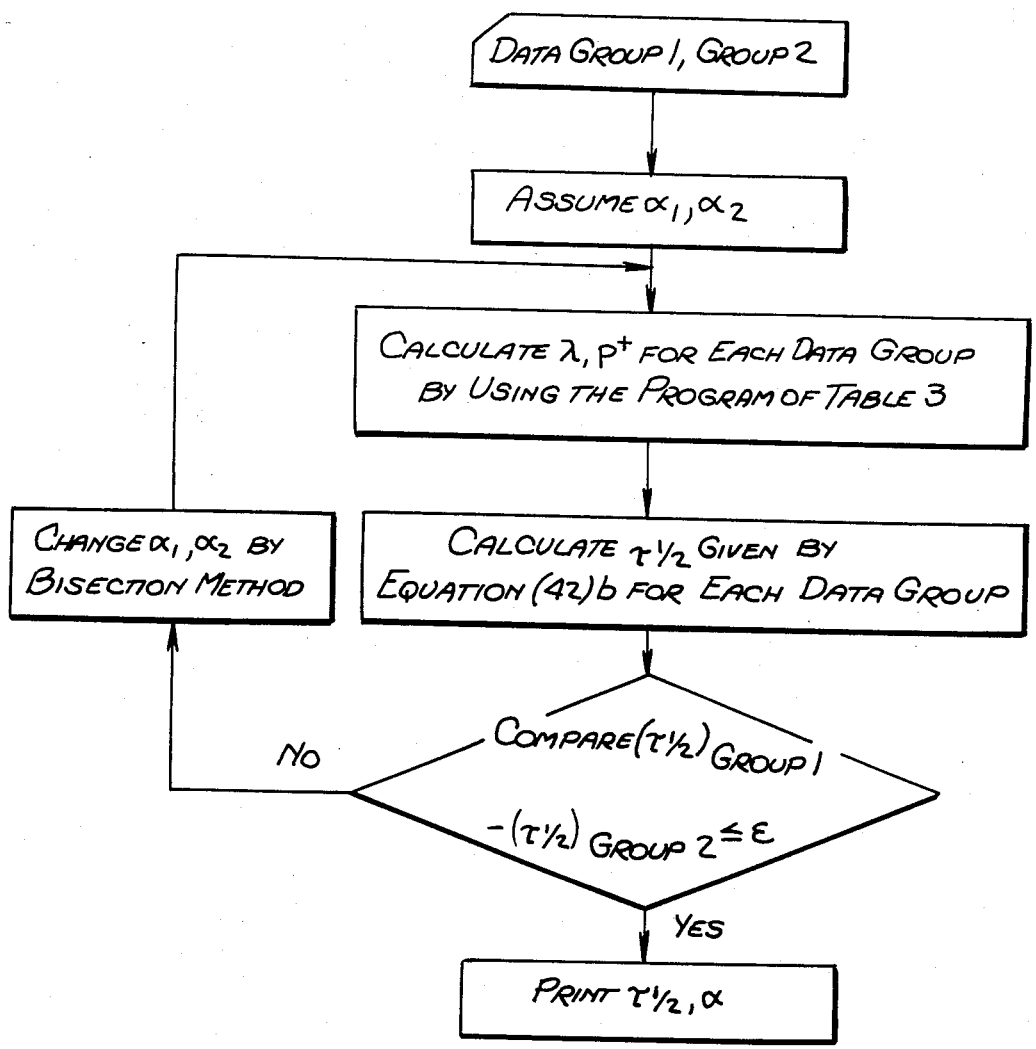
FIG. 7 is the flow chart for calculating $\alpha$ and $\rho_{\frac{1}{2}}$ according to the Ellis model.

The value for λ from two groups of data may also be determined according to the Ellis model by using the calculations according to the flow chart presented in FIG. 7.

Sodium carboxymethylcellulose (CMC) 7H4 (from Hercules Inc.) 10,000 and 15,000 wppm (ppm by weight) solutions, Carbopol 960 (from B. F. Goodrich) 1,750 and 2,000 wppm solutions were used. The solutions were prepared by dissolving the polymer powder in distilled water. The temperature was controlled at 25° C.

The viscosities of the solutions were also obtained by using the Rotating Cylinder Viscometer (RTN) and Capillary Tube Viscometer (CTV).

The experimental deviations of the three systems were found to be ±2% for the falling needle viscometer in contrast to ±3% for the falling cylinder viscometer and ±2% for the capillary tube viscometer.

The data obtained were plotted on log-log gragh paper. The results show good agreement between the results obtained for the falling needle viscometer, the rotating cylinder viscometer and the capillary tube viscometer. However, it can be observed that the falling needle viscometer of the present invention is particularly suitable for measuring viscosity at low and intermediate shear rates.

It is understood that the sccpe of the invention is not to be limited to the preferred embodiments described herein to illustrate the present invention.

We claim:

1. An apparatus for the determining viscosity of fluids comprising:
   a. A cylinder, of diameter D cm., for holding the fluid for which the viscosity is to be determined;
   b. Means for measuring axial displacement a predetermined distance, L cm., along the vertical axis of the cylinder, remote from the top and bottom by a distance of at least D cm.;
   c. A needle, made of tubing with rigid side walls the density of which can be adjusted with thin metal wiring to produce a velocity of fall of almost 0 to about 10 cm. per sec. and sealed hemispherically at both ends, having a diameter d cm., wherein b=D/d is at least 5, and a length of l cm., wherein l/D is at least 2.5;
   d. Means engaging the top of the cylinder for guiding said needle so that the needle will fall along the axis of said cylinder;
   e. Means for maintaining a constant temperature in the cylinder; and
   f. Device for measuring the time of fall of the needle between the predetermined distance marked on the cylinder.

2. An apparatus according to claim 1 further comprising a needle collector placed on the bottom of the cylinder for easy retreival of the needles.

3. A needle collector of the apparatus according to claim 2 having a cylindrical side wall, a bottom and a fine net covering the bottom, the cylindrical side walls having holes along the top edge and the bottom having a deflector in the form of a point centrally located and drain holes.

4. An apparatus according to claim 1 wherein the cylinder is a double walled cylinder with an inlet and outlet for the circulation of a constant temperature fluid to maintain a constant temperature in the system.

5. An apparatus according to claim 2, wherein the cylinder is a double walled cylinder with an inlet and outlet for the circullation of a constant temperature fluid to maintain a constant temperature in the system.

6. An apparatus according to claim 1 wherein the needle is made of the group of materials comprising glass aluminium and stainless steel tubing and the density is adjusted with solder wiring.

7. An apparatus according to claim 1 wherein the diameter (d) of the needle is about 0.05 to 0.5 cm. and the length l of the needle is about 1 cm to about 20 cm.

8. An apparatus according to claim 1 wherein the diameter (d) of the needle is about 0.16 cm and the length of the needle is about 10 cm.

9. An apparatus according to claim 1 wherein the means for measuring the time of fall is an electrophoto device connected to a chronometer.

10. An apparatus according to claim 1 wherein the means for measuring the time of fall is a magnetic sensing device connected to a chronometer.

11. A needle, for measuring the viscocity of Newtonian and non-newtonian fluids in a cylinder of diameter D cm, made of tubing with rigid side walls, the density of which can be adjusted with thin metal wiring to produce a velocity of fall of almost 0 to about 10 cm per sec. and capable of being sealed hemispherically at both ends, having a diameter d cm. wherein b=D/d is at least 5, and a length of l cm., wherein l/D is at least 2.5.

12. A needle according to claim 11 wherein b=D/d is at least 10.

13. A needle according to claim 11 wherein b=D/d is at least 24.

14. A needle according to claim 11 wherein d is about 0.05 cm. to about 0.5 cm. and l is about 1 cm. to about 20 cm.

15. A needle according to claim 11 wherein d is about 0.16 cm. and l is about 10 cm.

16. A method for determining the viscosity of a Newtonian fluid using the apparatus of claim 1 wherein the method comprises:
   a. Filling a cylinder with a diameter D according to the apparatus described above with a fluid for which the viscosity is desired.
   b. Placing means for guiding said needle in the form of a funnel with bottom and spacer and holes aligned vertically therein on top of the cylinder;
   c. Activating means for maintaining a constant temperature in the fluid;
   d. Inserting a needle having a diameter d and a length l, wherein b=D/d is at least 5 and l/D is at least 2.5 and adjusted to produce a velocity of fall of almost 0 to about 10 cm. per sec. into the hole in the spacer of the funnel, and held in position until the temperature of the needle is the same as that of the fluid;
   e. Allowing the needle to fall through the hole on bottom of the funnel;
   f. Measuring the time, t sec., taken for the needle to fall between the predetermined distance, L cm., marked on the cylinder, and
   g. Calculating the viscosity using the following equations:

$$\eta = \frac{(\rho_s - \rho_f)gd^2}{8V_\infty} \cdot \frac{b^2(\ln b - 1) + (\ln b + 1)}{b^2 + 1}$$

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

where $\rho_s$ is the density of the needle, $\rho_f$ is the density of the fluid, g is the gravity constant, d is the diameter of the reedle, L is the predetermined distance of fall, t is the time of fall and b=D/d 17. A method for determining the viscosity of a non-Newtonian fluid using the apparatus of Claim 1 wherein the method comprises:
   a. Filling a cylinder with a diameter D according to the apparatus described above with a fluid for which the viscosity is desired;
   b. Placing means for guiding a needle in the form of a funnel with bottom and spacer and holes aligned vertically therein on top of the cylinder;
   c. Activating means for maintaining a constant temperature in the fluid;
   d. Inserting a needle having a diameter d and a length l, wherein b=D/d is at least 5 and l/D is at least 2.5 and adjusted to produce a velocity of fall of almost 0 to about 10 cm. per sec. into the hole in the spacer of the funnel, and held in position until the temperature of the needle is the same as that of the fluid;
   e. Allowing the needle to fall through the hole on bottom of the funnel;
   f. Measuring the time, t sec., taken for the needle to fall between the predetermined distance, L cm., along the vertical axis of the cylinder, and
   g. Calculating the viscosity using the following equations where:
   (i) $V_\infty$ is calculated as follows:

$$V_\infty = \frac{L}{t} \cdot \frac{1 + \left(\frac{d}{C_w(l-d)}\right)\left(\frac{3}{2}\right)\left(\frac{b^2(\ln b - 1) + (\ln b + 1)}{b^2 + 1}\right)}{1 + \frac{2d}{3(l-d)}}$$

$$C_w = 1 - \frac{2.104}{b} + \frac{2.09}{b^3}$$

where L is the predetermined distance marked on the cylinder and t is the time taken for the needle to fall through L cm;

(ii) The flow index, n, where:

$$n = \frac{d[\ln(\rho_s - \rho_f)]}{d[\ln V_\infty]}$$

is determined from the slope of log $(\rho_s - \rho_f)$ vs log $V_\infty$;

(iii) n is then used to determine the position of maximum velocity, by solving the integral equation:

$$\int_k^\lambda \left(\frac{\lambda^2}{r} - r\right)^{1/n} r^2 dr - \int_k^\lambda \left(r - \frac{\lambda^2}{r}\right)^{1/n} r^2 dr = 0$$

where k = 1/b and r is the ratio of the coordinate to R, the radius of the cylinder;

(iv) $\lambda$ and n are then used to solve the equation to obtain $p^+$:

$$\int_k^\lambda \left(\frac{\lambda^2}{r} - r\right)^{1/n} dr - \int_\lambda^1 \left(r - \frac{\lambda^2}{r}\right)^{1/n} dr = \frac{1}{p^+};$$

(v) The fluid consistancy K is calculated from the equation:

$$K = \left(\frac{R}{V_\infty}\right)^n \left(\frac{1}{b\lambda}\right)^2 \left(\frac{1}{p^+}\right)^n \frac{gR(\rho_s - \rho_f)}{2}$$

where g is the gravity constant, R is the radius of the cylinder;

(vi) The shear rate at the needle wall is then calculated from:

$$\gamma_w = \frac{2V_\infty}{d} \cdot p^+ \cdot \frac{1}{b}\left(\lambda^2 b - \frac{1}{b}\right)^{1/n};$$

(vii) The shear stress at the needle wall is then calculated using the equation:

$$\tau_w = \frac{gd(\rho_s - \rho_f)}{4}\left\{\left(\frac{1}{\lambda b}\right)^2 - 1\right\};$$

(viii) The viscosity, $\eta$, is then calculated as:

$$\eta = \frac{-\tau_w}{\gamma_w}$$

18. A method according to claim 16 where the step of calculating the viscosity is accomplished by using a computer to obtain solutions to the equations.

19. A method according to claim 17 where the step of calculating the viscosity is accomplished by using a computer to obtain solutions to the equations.

* * * * *